United States Patent
Hofer Kraner et al.

(10) Patent No.: US 10,736,782 B2
(45) Date of Patent: Aug. 11, 2020

(54) FACE PROTECTOR

(71) Applicant: Optrel AG, Wattwil (CH)

(72) Inventors: Ramon Hofer Kraner, Herisau (CH); Daniel Iranyi, Steinhausen (CH); Leo Keller, Ruti ZH (CH); Arno Lenzi, Zurich (CH); Tom Staubli, Zurich (CH); Uwe Werner, Hutten (CH)

(73) Assignee: OPTREL HOLDING AG, Appenzell (CH)

( * ) Notice: Subject to any disclaimer, the term of this patent is extended or adjusted under 35 U.S.C. 154(b) by 730 days.

(21) Appl. No.: 14/448,291

(22) Filed: Jul. 31, 2014

(65) Prior Publication Data
US 2015/0033431 A1    Feb. 5, 2015

(30) Foreign Application Priority Data

Aug. 5, 2013 (CH) ...................................... 1353/13
Sep. 6, 2013 (EP) ...................................... 13405108
Apr. 23, 2014 (CH) ...................................... 0616/14

(51) Int. Cl.
*A61F 9/06*        (2006.01)

(52) U.S. Cl.
CPC .................... *A61F 9/067* (2013.01)

(58) Field of Classification Search
CPC .. A61F 9/045; A61F 9/06; A61F 9/061; A61F 9/064; A61F 9/067; A61F 9/029;
(Continued)

(56) References Cited

U.S. PATENT DOCUMENTS 1,416,848 A * 5/1922 Lightfield ............... A61F 9/061
                                                        2/10
2,086,208 A * 7/1937 Brekelbaum ........... A61F 9/061
                                                        2/11
(Continued)

FOREIGN PATENT DOCUMENTS

CA     2 184 929    3/1998
CA     2184929     3/1998
(Continued)

OTHER PUBLICATIONS

European Search Report dated Jan. 26, 2015, Application No. 14179317.4, English Translation Included.
(Continued)

*Primary Examiner* — Clinton T Ostrup
*Assistant Examiner* — Andrew Wayne Sutton
(74) *Attorney, Agent, or Firm* — Rankin, Hill & Clark LLP

(57) ABSTRACT

A face protector for protecting a worker's eyes and face comprises an auto-darkening filter unit which in turn comprises a filter pane or ADF pane and an electronics unit driving the ADF pane, the electronics unit being configured to switch the ADF pane automatically from a transparent state to a darkened state. A hard shell unit comprises a shell carrying an ADF unit with the ADF and being shaped to protect a wearer's face, the shell being manufactured of a plastic material. A soft shell unit comprises a cap for protecting the crown of the wearer's head and a neck protector for protecting the wearer's neck, the soft shell unit being made of a combination of flexible fabric with support elements.

20 Claims, 4 Drawing Sheets

(58) Field of Classification Search
CPC .. G02C 3/02; A42B 3/22; A42B 3/222; A42B 3/225
USPC .......... 2/8.8, 8.7, 8.2, 8.3, 8.4, 6.3, 6.5, 424, 2/422, 468; 351/155
See application file for complete search history.

(56) References Cited

U.S. PATENT DOCUMENTS

| | | | | |
|---|---|---|---|---|
| 2,105,071 | A * | 1/1938 | Bowers | A61F 9/061 16/293 |
| 2,544,457 | A * | 3/1951 | Harrington | A61F 9/06 2/8.1 |
| 2,578,171 | A * | 12/1951 | Bub | A42B 3/225 16/340 |
| 2,638,592 | A * | 5/1953 | Olson | A61F 9/068 2/8.7 |
| 2,817,087 | A * | 12/1957 | Rush | A61F 9/06 2/8.1 |
| 3,298,031 | A * | 1/1967 | Morgan | A41D 13/1184 2/427 |
| 3,748,658 | A * | 7/1973 | Albright | A42B 3/226 2/10 |
| 3,873,804 | A * | 3/1975 | Gordon | A61F 9/067 2/8.8 |
| 3,921,222 | A * | 11/1975 | Hollman | A63B 71/12 2/463 |
| 4,076,373 | A * | 2/1978 | Moretti | A42B 3/26 2/434 |
| 4,080,664 | A * | 3/1978 | Morris | A61F 9/068 128/206.15 |
| 4,114,198 | A * | 9/1978 | Sands | A61F 9/06 2/427 |
| 4,180,868 | A * | 1/1980 | Snow | A42B 3/105 2/172 |
| 4,193,132 | A * | 3/1980 | Peterson | A61F 9/06 2/8.1 |
| 4,210,972 | A * | 7/1980 | Baclit | A42B 1/062 2/10 |
| 4,373,212 | A * | 2/1983 | West | A61F 9/065 2/8.7 |
| 4,602,385 | A * | 7/1986 | Warren | A41D 13/0153 2/2.14 |
| 4,686,710 | A * | 8/1987 | Marston | A41D 13/0512 2/2.5 |
| 4,724,550 | A * | 2/1988 | Fox | A42B 1/12 2/424 |
| 4,726,074 | A * | 2/1988 | Baclit | A42B 1/247 2/10 |
| 4,853,973 | A * | 8/1989 | Boochard | A61F 9/06 2/434 |
| 4,863,244 | A * | 9/1989 | Fuerthbauer | A61F 9/067 2/431 |
| 4,965,887 | A | 10/1990 | Paoluccio et al. | |
| 5,083,319 | A * | 1/1992 | Grilliot | A62B 17/003 2/81 |
| 5,113,526 | A * | 5/1992 | Wang | A43B 7/32 2/10 |
| 5,119,516 | A * | 6/1992 | Broersma | A42B 3/066 2/411 |
| 5,125,113 | A * | 6/1992 | Yun | A42B 1/205 2/10 |
| 5,477,563 | A * | 12/1995 | Gentes | A42B 3/062 2/411 |
| 5,544,361 | A * | 8/1996 | Fine | A42B 1/062 2/10 |
| 5,749,096 | A * | 5/1998 | Fergason | A61F 9/06 2/410 |
| 5,819,318 | A * | 10/1998 | Tse | A42B 1/22 2/182.1 |
| 5,924,129 | A * | 7/1999 | Gill | A42B 1/062 2/10 |
| 6,035,451 | A * | 3/2000 | Burns | A42B 3/10 2/424 |
| 6,295,652 | B1 * | 10/2001 | Mazur | A42B 3/0473 2/422 |
| 6,614,409 | B1 * | 9/2003 | Bae | A61F 9/065 2/8.7 |
| 6,996,852 | B1 * | 2/2006 | Cabrera | A42B 1/062 2/171 |
| 7,343,630 | B2 * | 3/2008 | Lee | A42B 1/067 2/175.6 |
| 7,945,297 | B2 | 5/2011 | Philipp | |
| D640,419 | S * | 6/2011 | Wright | D29/110 |
| D640,421 | S * | 6/2011 | Wright | D29/122 |
| 8,042,958 | B2 | 10/2011 | Sundell | |
| D667,173 | S * | 9/2012 | Juhlin | D29/122 |
| D667,591 | S * | 9/2012 | Juhlin | D29/122 |
| D674,150 | S * | 1/2013 | Juhlin | D29/122 |
| 8,457,949 | B2 * | 6/2013 | Huh | A61F 9/067 2/8.2 |
| 8,490,214 | B2 * | 7/2013 | Crye | F41H 1/04 2/2.5 |
| 9,610,198 | B2 * | 4/2017 | Hofer-Kraner | A61F 9/061 |
| 2003/0000001 | A1 * | 1/2003 | McDonald | A62B 18/02 2/6.3 |
| 2004/0098789 | A1 * | 5/2004 | Carey | A42B 1/046 2/173 |
| 2004/0117888 | A1 * | 6/2004 | Wang-Lee | A42B 3/20 2/8.1 |
| 2004/0177426 | A1 * | 9/2004 | Wang-Lee | A61F 9/061 2/63 |
| 2005/0166303 | A1 * | 8/2005 | Aaron | A41D 13/0512 2/422 |
| 2005/0204446 | A1 * | 9/2005 | Wright | A61F 9/029 2/9 |
| 2006/0010550 | A1 * | 1/2006 | Cheng | A42B 3/225 2/9 |
| 2006/0080761 | A1 * | 4/2006 | Huh | A42B 3/04 2/424 |
| 2006/0101555 | A1 * | 5/2006 | Curran | A61F 9/045 2/171.3 |
| 2006/0107431 | A1 * | 5/2006 | Curran | A61F 9/045 2/7 |
| 2006/0272067 | A1 * | 12/2006 | Gagnon | A41D 13/11 2/9 |
| 2006/0285330 | A1 * | 12/2006 | Sundell | A61F 9/067 362/293 |
| 2007/0079417 | A1 * | 4/2007 | Huh | A61F 9/065 2/8.2 |
| 2007/0081250 | A1 * | 4/2007 | Garbergs | A61F 9/061 359/601 |
| 2007/0192946 | A1 * | 8/2007 | Wright | A61F 9/029 2/424 |
| 2007/0220649 | A1 * | 9/2007 | Huh | A61F 9/025 2/9 |
| 2008/0060102 | A1 * | 3/2008 | Matthews | A61F 9/061 2/8.2 |
| 2009/0000001 | A1 * | 1/2009 | Huh | A61F 9/067 2/8.7 |
| 2009/0094721 | A1 * | 4/2009 | Becker | A61F 9/067 2/8.8 |
| 2009/0231423 | A1 * | 9/2009 | Becker | A61F 9/06 348/82 |
| 2010/0107318 | A1 * | 5/2010 | Asta | A42B 3/105 2/424 |
| 2010/0132086 | A1 * | 6/2010 | Huh | A61F 9/061 2/8.2 |
| 2010/0223707 | A1 * | 9/2010 | Moyses | A42B 3/225 2/8.2 |
| 2011/0010815 | A1 * | 1/2011 | Huh | A61F 9/067 2/8.8 |
| 2011/0023205 | A1 * | 2/2011 | Braendle | A61F 9/06 2/8.7 |
| 2011/0030114 | A1 * | 2/2011 | Merikoski | A42B 3/225 2/8.7 |
| 2011/0119801 | A1 * | 5/2011 | Wright | A61F 9/064 2/8.2 |

(56) References Cited

U.S. PATENT DOCUMENTS

| | | | |
|---|---|---|---|
| 2011/0179541 A1* | 7/2011 | Wright | A61F 9/064 2/12 |
| 2011/0185480 A1* | 8/2011 | Braendle | A61F 9/06 2/421 |
| 2011/0247119 A1* | 10/2011 | Cheng | A61F 9/06 2/8.5 |
| 2011/0271429 A1* | 11/2011 | Nakayama | A42B 3/225 2/424 |
| 2012/0204303 A1* | 8/2012 | Seo | A61F 9/023 2/12 |
| 2012/0216340 A1* | 8/2012 | Asta | A42B 3/105 2/422 |
| 2013/0014316 A1* | 1/2013 | Castro | A41D 13/1184 2/424 |
| 2013/0047324 A1* | 2/2013 | Park | A61F 9/025 2/434 |
| 2013/0081190 A1* | 4/2013 | Wu | A61F 9/06 2/8.7 |
| 2013/0097760 A1* | 4/2013 | Feinberg | G02B 7/006 2/8.2 |
| 2013/0291271 A1* | 11/2013 | Becker | G06F 3/005 2/8.2 |
| 2013/0312156 A1* | 11/2013 | Dean | A42B 1/18 2/172 |
| 2013/0340141 A1* | 12/2013 | Huh | A61F 9/067 2/8.8 |
| 2014/0007312 A1* | 1/2014 | Wright | A61F 9/064 2/8.2 |
| 2014/0013479 A1* | 1/2014 | Magnusson | A61F 9/067 2/8.7 |
| 2014/0020147 A1* | 1/2014 | Anderson | A61F 9/06 2/8.2 |
| 2014/0053307 A1* | 2/2014 | Cheng | A61F 9/06 2/8.2 |
| 2014/0059730 A1* | 3/2014 | Kim | A61F 9/06 2/8.2 |
| 2014/0082810 A1* | 3/2014 | Daniels | A61F 9/067 2/8.2 |
| 2014/0168546 A1* | 6/2014 | Magnusson | A41D 13/1184 349/14 |
| 2014/0215673 A1* | 8/2014 | Lilenthal | A61F 9/065 2/12 |
| 2014/0298557 A1* | 10/2014 | Townsend, Jr. | A61F 9/06 2/8.2 |
| 2014/0320771 A1* | 10/2014 | Keller | A61F 9/067 349/14 |
| 2015/0033430 A1* | 2/2015 | Hofer Kraner | A61F 9/06 2/8.2 |
| 2015/0033431 A1* | 2/2015 | Hofer Kraner | A61F 9/067 2/8.8 |
| 2015/0135389 A1* | 5/2015 | Yang | A61F 9/067 2/8.8 |
| 2015/0264992 A1* | 9/2015 | Happel | A42B 3/04 2/422 |
| 2015/0342282 A1* | 12/2015 | Daniels | A42B 3/16 2/8.2 |
| 2015/0359677 A1* | 12/2015 | Sommers | A42B 3/085 2/8.2 |
| 2015/0359679 A1* | 12/2015 | Sommers | A61F 9/064 2/8.5 |
| 2016/0081856 A1* | 3/2016 | Hofer-Kraner | A61F 9/061 2/8.3 |
| 2016/0163221 A1* | 6/2016 | Sommers | A61F 9/06 434/234 |
| 2016/0183622 A1* | 6/2016 | Patel | A42B 3/222 2/424 |

FOREIGN PATENT DOCUMENTS

| | | | | |
|---|---|---|---|---|
| CN | 2098909 | | 3/1992 | |
| CN | 101505697 | | 8/2009 | |
| DE | 20 2005 009 226 | | 12/2005 | |
| EP | 1 789 835 | | 12/2009 | |
| EP | 2 275 061 | | 1/2011 | |
| EP | 2 323 509 | | 9/2012 | |
| WO | WO 9427180 A1 * | 11/1994 | | A61F 9/06 |
| WO | 96/22033 | | 7/1996 | |
| WO | WO 9622033 A1 * | 7/1996 | | A42B 1/062 |
| WO | 97/28770 | | 8/1997 | |
| WO | WO 9728770 A1 * | 8/1997 | | A61F 9/06 |
| WO | 2006/061007 | | 6/2006 | |
| WO | WO 2007083900 A1 * | 7/2007 | | A61F 9/06 |
| WO | 2008/024555 | | 2/2008 | |
| WO | WO 2009099257 A1 * | 8/2009 | | A61F 9/061 |
| WO | 2011/063287 | | 5/2011 | |

OTHER PUBLICATIONS

Chinese Office Action dated May 10, 2017, Application No. 201410524334.9, English translation included, 15 pages.

European Office Action dated Jul. 13, 2018, Application No. 14 179 317.4, 7 pages.

* cited by examiner

FACE PROTECTOR

FIELD OF THE INVENTION

The invention relates to the field of face protection for welders and workers in electrical installations and in particular to a face protector for protecting a welder's eyes and face from glare and welding splatter and for protection against the effects of fault arcs.

DESCRIPTION OF RELATED ART

U.S. Pat. No. 5,544,361 describes a lightweight headgear for protecting a wearer's face from ultraviolet radiation. It includes a face shield with shield segments that, in a retracted position, nest with each other. The face shield can be attached to a baseball cap or to eyeglasses.

U.S. Pat. No. 4,965,887 describes a face protector for splash and splatter protection in the medical field. It includes a bent rectangular plastic shield attached to a hood impermeable to fluids. It can be attached to a baseball cap or to eyeglasses.

U.S. Pat. No. 4,724,550 describes a cap and goggles combination including a rubber cap and a face glass to keep hair and face dry when swimming. The face glass is curved and includes a cutout resting on the bridge of the wearer's nose.

EP 1789835 B1 describes an optically decentered face shield in which an optical centre of the face shield is displaced away from the normal straight ahead line of sight toward an activity specific line of sight, e.g. for one eye and for a particular sports activity.

U.S. Pat. No. 8,042,958 describes a welding mask with an automatic darkening filter with automatic power management. Power to the filter is turned on or off depending on movement of the device, detected by a motion sensor.

U.S. Pat. No. 7,945,297 describes an audio headset including a capacitive sensor to detect the presence of a user. Power consumption is reduced when a user is not present.

Welding protection equipment has made significant progress during the last couple of years. Active, opto-electronic auto-darkening welding filters allow hands-free operation and the uninterrupted control of the different welding processes. Auto-darkening welding filters (ADF) have gained the ability to automatically select the appropriate shade number according to the intensity changes of the welding arc, and, the switching speed from the transparent to the attenuated state has increased by a factor of 40. The protection of the eyes and the skin of the welder against optical radiation is represented by minimum requirements that today are fulfilled by almost every single product available. Accidents and frequent arc eyes are becoming the exception.

However, the basic concepts underlying anti-glaring protection helmets themselves have not changed much over the last hundred years: A very stiff and bulky face protector is mounted on a harness or on a headgear that is then fixed on the head by physical friction. The number of parts required and the necessity for flipping up the helmet create a framework in which a relatively heavy optical system, in most cases built as replaceable cartridge, leads to a tunnel-like viewing characteristic and adds weight, creating neck strain and fatigue. The result, in combination with the tensions created by the tight fit of the headgear on the head and the large distance of the face protector from the head, is discomfort, headaches and operational hindrance to do the welding job efficiently, especially in confined space environments.

In electrical installations, fault arcs can occur due to mistakes made by a worker. Low-voltage installations are affected by unipolar phase-to-earth faults or by bi-polar phase-to-phase faults. In a high-voltage environment a fault-arc incident can already occur because of a too small air gap. The effects of a fault arc are devastating: The explosive energy shock can generate temperatures of up to 20,000° C., an acoustic shock of up to 140 dB, a pressure wave of up to 20-30 t/m2, a plasma wave of high chemical aggressiveness and a high amount of electromagnetic radiation in the entire spectral range from the near UV to the far IR. The danger to persons working in the direct vicinity of a fault-arc incident are second and third-degree burns of the skin, danger of flying objects provoked by the pressure wave and the exposure to toxic components of the pyrolysis of metals, insulation and other surrounding materials as well as fumes and smoke. The electromagnetic radiation in the UV and in the visual spectral range leads to a very high risk of eye damage, leading to loss of balance and orientation and further injury.

State-of-the-art technology and materials do not provide perfectly safe protection equipment means against fault-arc today. Weight and bulkiness of the equipment limit the acceptance of the wearer and goggles as well as face-shields often restrict the field-of-view, especially in con-fined environments such as electrical cabinets. Even the temperature resistance of the most advanced materials does not adequately protect against the high thermal flux of fault-arcs today.

DE 202005009226 U1 discloses a fault-arc protection device with a transparent, passive PC or Acetate visor. The unit does not protect from the effects of the strong light flash in the visual range of the spectrum at all and the temperature resistance of the clear visor is very limited. The time, the protector withstands the effects of fault-arcs, is estimated to be about 20% of the required protection time of 0.5 seconds.

US 2011/0030114 A1 explicitly adds UV protection by using UV absorbing thermoplastic materials such as Polycarbonates and increases the lens thickness from 1 to 4 mm for increased robustness and better absorbance. However, the user of such a protective device is still only passively protected and therefore extremely exposed to the arc flash of the fault-arc.

EP 2 323 509 B1 adds commercially available UV and IR absorbing/reflecting plastic films laminated to the transparent visor. It can be assumed that the obtained values do not fulfil the stringent requirements of current eye protection standards (EN 166, EN 169). In addition, the proposed protector is again passive and does therefore not protect from the effects of the strong electromagnetic emission of the fault-arc in the visible spectral range.

Fault-arc protection equipment has made significant progress with regard to heat resistance and the passive protection against the effect of fault-arc has improved in the electromagnetic radiation range of the UV and partially also in the IR spectral range. However, the most important spectral range of the electromagnetic radiation with regard to a clear vision of an electrician during his demanding operational activity, the visible spectral range, remained almost unprotected and the arc-flash has only passively been reduced to ca. 50% or more by means of using dyes that substantially reduce the brightness of the visor and therefore affect visibility and safety under normal conditions. Current passive protection devices against intense arc-flashes provide limited IR protection and almost no protection against the visible spectrum of the electromagnetic radiation. This represents a high risk of permanent damage to the eye by the visual flash or by the still excessive IR radiation. In addition, the user of such equipment may be temporarily blinded and therefore suffer further injuries from stumbling, coming into contact with electrical conductors, etc.

BRIEF SUMMARY OF THE INVENTION

It is an object of the invention to create a welding protection mask which allows for a larger field of view than commonly known welding masks.

It is a further object of the invention to create a protection mask which is light weight and is comfortable to carry, in particular by having an improved distribution of weight.

It is a further object of the invention to create a protection mask which is easy to put on and take off, increasing the efficiency of the welding process.

It is a further object of the invention to create a protection mask which protects the wearer against the effects of an electric fault arc.

It is a further object of the invention to create a protection mask against fault arcs exhibiting improved protection of the eye in the UV and the visible spectral range.

It is a further object of the invention to create a protection mask against fault arcs that avoids the "chimney effect" in which a hot air pressure wave flows into and through the protective device, injuring the wearer at the chest and neck area.

At least one of these objects is at least partially achieved by face protectors according to the patent claims.

The face protector includes an auto-darkening filter (ADF) unit which in turn includes a filter pane or ADF pane and an electronics unit driving the ADF pane, the electronics unit being configured to switch the ADF pane automatically from a transparent state to a darkened state, for example when a welding operation takes place or when the flash of an fault arc is detected. The face protector further includes a hard shell unit and a soft shell unit attached to each other. The hard shell unit includes a shell carrying an ADF unit with the ADF and being shaped to protect a wearer's face, the shell being manufactured of a plastic material. The soft shell unit includes a cap for protecting the crown of the wearer's head and a neck protector for protecting the wearer's neck, the soft shell unit being made of a combination of flexible fabric with support elements.

In this manner, soft and hard materials are combined, providing a face (and eye) protector or welding cap or welding face protector cap with increased comfort, as compared to conventional welding masks, and simplifying a fast and easy putting on and off functionality of the face protector. By using different material means, high structural stability and impact and process temperature resistance can be achieved with at the same time low cost manufacturing opportunities.

The face protector does not require a separate headgear for holding the protective parts. Rather, the elements for supporting the weight of the protective parts, when in use, are integrated in the soft shell unit and in particular in the cap.

The face protector can have one-size-fits-all capability. It allows close working distance to the weld (e.g. for shipyard applications) or other work area and supports confined space applications. Overall, the efficiency of a worker can be enhanced by these factors without compromising on safety, comfort, fatigue and long-term physical health.

The hard shell unit can be realised with different choices of material, depending on requirements:

high structural stability can be achieved by employing injection moulded flame retardant polyamide (PA) structures.

low cost manufacturability can be achieved by employing thermoformed flame retardant polycarbonate structures (PC).

high resistance against impact and process temperature can be achieved by employing thermoformed epoxy materials which are reinforced by glass fibre materials.

The soft shell unit can be realised with different choices of material, depending on requirements:

low cost manufacturability can be achieved by employing inherently flame retardant fabric materials.

low cost manufacturability can be achieved by employing impregnated flame retardant cotton materials.

high resistance against process temperature can be achieved by employing flame retardant leather materials.

high resistance against process temperature can be achieved by employing flame retardant polyimide materials (PI).

In accordance with the invention, the face protector is configured such that when it is worn by a wearer, a distance (d) from the wearer's pupils to the ADF pane lies in the range of 30 mm to 50 mm, in particular in the range of 35 mm to 45 mm. In certain embodiments, a vertical extension h of the transparent part of the ADF pane is at least 40 mm, in particular at least 45 mm. In certain embodiments, a horizontal extension w of the transparent part of the ADF pane is at least 100 mm, in particular at least 110 mm. In certain embodiments, a lower edge of the ADF pane includes a concave cutout for accommodating the wearer's nose.

Such measures, alone or in combination, allow one to achieve on the one hand a close-to-the-eye configuration with a large field of view, compared to current products, and on the other hand a compact and low weight design.

Furthermore, since the front parts are lightweight and closer to the wearer's face, the distribution of the weight of the face protector can be better balanced than in conventional protective or welding mask solutions. This reduces fatigue and neck strain and makes the face protector comfortable to carry.

In further accordance with the invention, the ADF pane is curved or spherical. For example, side portions of the ADF pane, relative to a central portion of the ADF pane, can curve backwards. That is, the side portions or lateral portions are curved in the direction of the wearer's face. By following the contour of the wearer's face the hard shell unit can be made even more compact and/or the field of view can be increased even more.

In further accordance with the invention, the hard shell unit includes a protective shield, the protective shield being attached by means of a releasable connection, the protective shield optionally being shaped such that a plurality of protective shields can be stacked on each other, nesting with each other. Such protective shields are subject to wear and damage and can therefore be user replaceable.

In further accordance with the invention, the cap is shaped in the manner of a baseball cap, including a rounded crown and a stiff visor projecting in front, the visor covering a transverse top section of the shell, the top section protecting a forehead space enclosed by the hard shell unit, and the visor supporting at least some of the weight of the hard shell unit when the face protector is worn by a wearer. This gives the face protector on the one hand an appealing form and on the other hand allows one to do away with a separate headgear for carrying the protective elements.

In further accordance with the present invention, the cap includes a stiffener (or reinforcement or bracing) sewn in or attached to the other parts of the cap, the stiffener holding up the visor against at least part of the weight of the hard shell unit. The stiffener can be considered stiff as compared to the fabric parts of the cap. The stiffener can be an integrally formed piece of a plastic material, extending over the area of the visor and extending toward the back of the cap around at least part of the horizontal circumference of the cap. The stiffener can extend around at least half of the horizontal circumference of the cap, or at least to the region of the wearer's ears.

In further accordance with the present invention, a top section, two side sections and a front section of the shell form a box-like structure that gives the shell structural stability, and wherein the front section includes a convex section that is curved in a convex shape, and a nose bridge section that is shaped to extend at an angle to the convex section, further stiffening the front section.

In further accordance with the present invention, the shell includes lateral side sections, a lower section of each side section being shaped to keep the neck protector distanced from the wearer's neck, thereby establishing a ventilation space between the neck protector and the wearer's neck. The ventilation space can lead to a breathing space in front of the wearer's mouth and nose, and to a forehead space in front of the wearer's forehead.

In further accordance with the present invention, the lower sections of the side sections are made of thinner material than the remaining sections of the side sections, and optionally also thinner than the other sections of the shell. This helps to reduce the overall weight of the mask.

In further accordance with the present invention, the side sections or at least the lower sections of the side sections are flexible and typically elastic, and can thereby be moved or flexed inwards, i.e. towards the wearer's face.

In further accordance with the present invention, the neck protector includes plastic stiffener elements that are joined to a flexible base material of the neck protector. The base material can be a textile or a flexible sheet of plastic. The stiffener elements are stiffer (i.e. less flexible) than the base material. The stiffener elements can be attached to the base material, e.g. by gluing, sewing, by fasteners etc. Alternatively or in addition, the stiffener elements can be attached to the base material by placing them in a pocket made of the base material, or more generally between two layers of the base material. Such stiffener elements or inserts can stabilize the softness or flexibility of the textile material, providing stability that prevents the textile structure from collapsing or being blown away and from thereby facilitating the so-called chimney effect In further accordance with the present invention, the side sections or at least the lower sections of the side sections are of a downward tapering shape or V-shape. This makes it easier for them to flex towards the wearer's face.

In further accordance with the present invention, the ADF pane is mounted on the shell by means of a frame section of the ADF frame, the frame section being attached to, in particular glued or welded to, the shell and holding the ADF pane in position between the frame section and the shell. This helps to reduce the overall weight of the mask since no separate frame or holder or cassette is used to hold the ADF pane or the entire ADF unit.

In further accordance with the present invention, the electronics unit is mounted on the shell by means of a cover section of the ADF frame, the cover section being attached to, in particular glued or welded to, the shell and holding the electronics unit in position between the cover section and the shell. This also helps to reduce the overall weight of the mask, again because there is no separate housing for the electronics unit.

In further accordance with the present invention, the frame section and the cover section are integrally shaped as a single piece. This simplifies production and assembly and makes connecting and sealing the ADF frame to the shell easier.

In further accordance with the present invention, the ADF frame includes at least one latch, the ADF frame is mounted at the inside of the shell with the latch reaching through a slot of the shell and forming a snap fit with the protective shield, holding the protective shield in place on the outer side of the shell. This further reduces the number of parts. It also makes for a better mechanical fit of the protective shield to the shell: If only the shell and the protective shield with their relatively stiff materials were involved, it would be more difficult or impossible to create a releasable snap action connection between the two.

In further accordance with the present invention, at least the frame section and the latch are integrally shaped as a single piece. This further simplifies assembly and reduces weight.

In summary, the reduction of weight of the face protector with respect to conventional protective or welding masks is achieved by a combination of at least some of the following measures
- the shell having a box-like structure;
- the shape of the front section and the nose bridge section;
- the lower sections of the side sections being thinner than the remaining parts of the side sections or of the shell;
- the ADF unit not being realised as a detachable and replaceable cassette;
- the ADF pane and optionally also the electronics unit being held in the shell in a sealed manner by the ADF frame, without any further mounting parts and without separate casings or frames for the ADF pane and or the electronics unit.

The balance of the face protector is improved by the reduction in weight and furthermore by at least a combination of at least some of the following measures:
- the shell being close to the wearer's face.
- the stiffener transferring part of the weight of the hard shell unit to the middle and to the back end of the cap.

The face protector avoids—in the case of arc fault protection with a corresponding blast—the chimney effect through the combination of hard and soft elements:
- the hard elements of the shell covering the face provide the main protection against heat and impact. The lateral side sections, and in particular the lower sections of the side sections, are flexible (and typically also elastic) and are pressed by the blast against the wearer's cheeks. This effect is supported by the tapering shape of the lower sections. This reduces the ventilation space between the neck protector and the wearer's neck and thus the chimney effect.
- the flexible elements of the soft shell unit, and in particular the neck protector, are pressed by the blast against the wearer's neck. This prevents the shock wave from the blast from entering the face protector.

The neck protector and the shell are affixed to each other, without gaps that would allow the shock wave to enter the face protector. Overall, the closed design and the selective flexibility provides improved protection against the chimney effect.

Note: as a rule, when in the present description reference is made to "upper", "lower", "horizontal", "vertical", "front" or "back" and the like, then this is understood to relate to the situation when the face protector is worn by a user, with the user's or wearer's head being in an upright position.

When plastic materials are mentioned, this as a rule includes fibre reinforced plastic materials.

BRIEF DESCRIPTION OF THE DRAWINGS

The subject matter of the invention will be explained in more detail in the following text with reference to exemplary embodiments which are illustrated in the attached drawings, which show.

In principle, identical parts are provided with the same reference symbols in the figures.

DETAILED DESCRIPTION OF THE INVENTION

Figure 1:
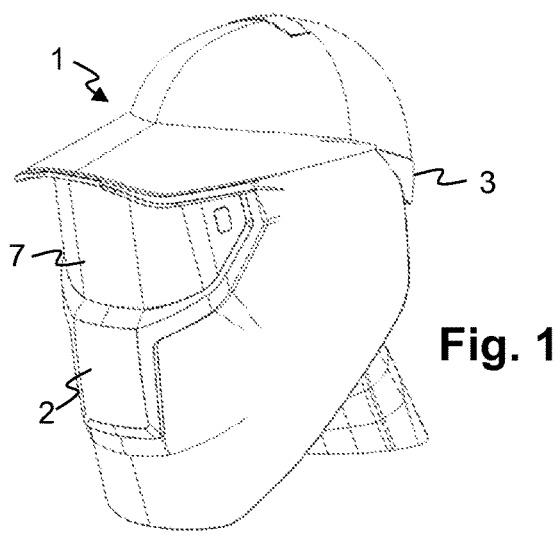
FIG. 1 illustrates a face protector 1.
Figure 2:
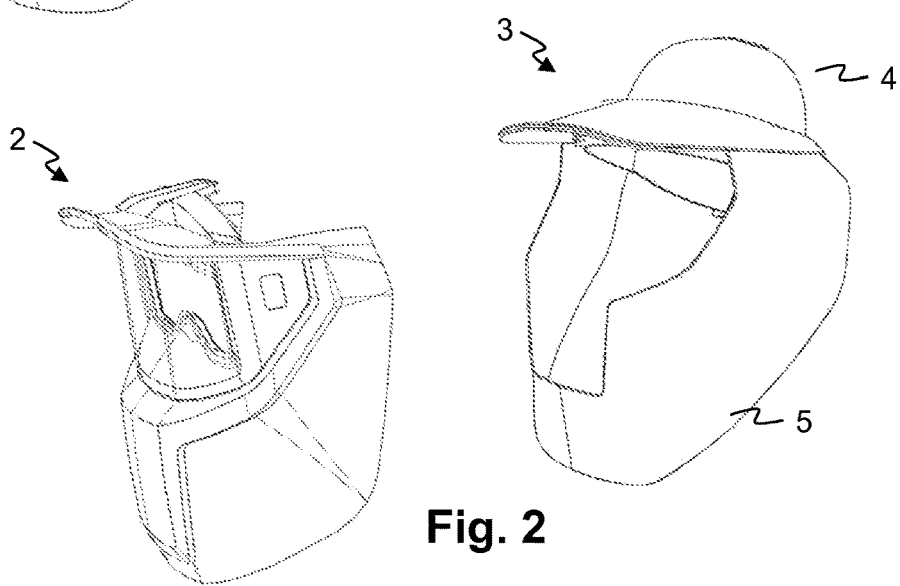
FIG. 2 illustrates main components of the face protector.
Figure 3:
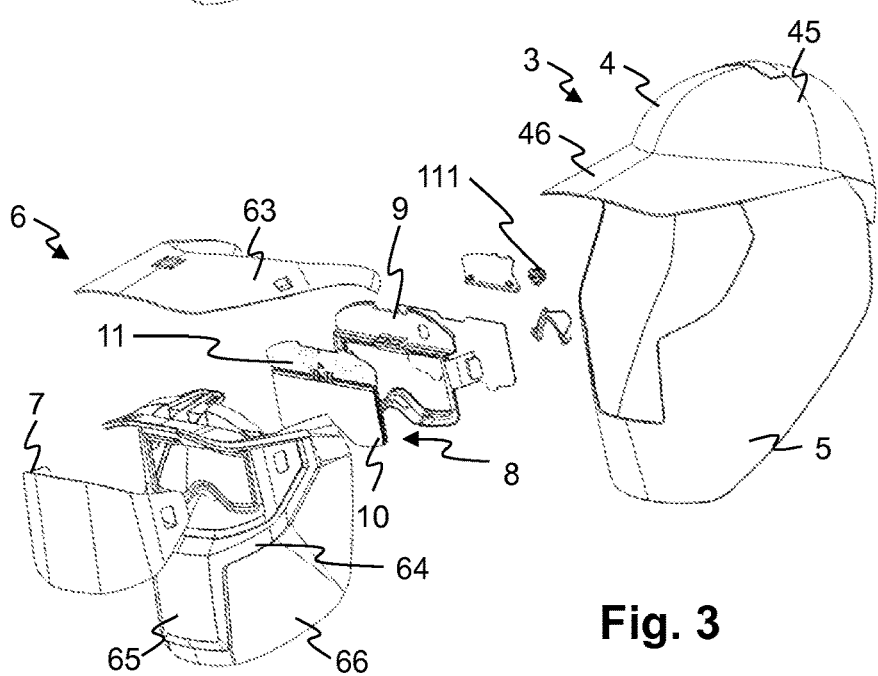
FIG. 3 illustrates further components of the face protector in an exploded view.

Components of a face protector according to an embodiment are explained with reference to FIG. 1 through FIG. 4. The face protector 1 includes a hard shell unit 2 and a soft shell unit 3. The hard shell unit 2 is made of a hard plastic material, for example from a material commonly used for welding masks, and is resistant to sparks and other influences occurring when welding or in the event of a fault arc. The shape of the hard shell unit 2 is adapted to cover and protect the user's face and head according to the relevant norms for welding masks. The soft shell unit 3 can be made mainly of a fabric, in particular of a functional fabric or textile material resistant to sparks, heat and other influences occurring when welding or in the event of a fault arc. The soft shell unit 3 includes a cap 4 and a neck protector 5. The cap 4 can be essentially shaped like a baseball cap, that is, including a rounded crown 45 and a stiff visor 46 or peak projecting in front. The hard shell unit 2 and soft shell unit 3 can be attached to each other and thus can be put on by the user or taken off together.

The hard shell unit 2 includes as main part a shell 6 carrying the other parts, in particular an Auto Darkening Filter (ADF) unit 8, an ADF frame 9 and a protective shield 7.

The ADF unit 8 in turn includes an ADF pane 10 with the actual filter pane, and an electronics unit 11. The electronics unit 11 typically includes a battery and/or solar cells, and one or more sensors and/or communication devices in order to detect when a welding operation or a bright light occurs that could damage or affect the user's eyes in other ways. The ADF pane 10 includes the actual ADF, typically an electro-optical filter. The ADF pane 10 can include a liquid crystal shutter driven by means of the electronics unit 11 to darken the shutter when the electronics unit 11 detects a welding process or flash of light occurring. The shutter reduces the visible transmittance (that is, the transmittance in the visible range of light), typically within less than 200 microseconds, to a shade number setting that provides protection to the eye against the effects of a welding arc or a fault arc flash. The visible transmittance of the filter is at least Shade Number 5, or, 2.2%, according to EN 169.

The ADF pane 10 can further include transparent protective plates, e.g. from polycarbonate or glass etc., between which the actual ADF is sandwiched. ADF shutters in general and associated welding or flash detection methods are known to the skilled person.

The ADF includes a liquid-crystal (LCD) shutter element sandwiched between layers of polarization films. The polarization films include ultraviolet (UV) absorbing means, which can be configured to fulfil the requirements of the German "Geprüfte Sicherheit" Standard GS-ET-29 (EN 166). The UV transmittance of the filter, e.g. at 313 nm, is typically less or equal than $3 \times 10^{-4}$%, according to EN 169.

The ADF includes cover plates, in particular glass plates, that have a non-conductive dielectric thin film coating on at least one inner side, reflecting and/or absorbing light in the infrared (IR) spectral range, and thereby protecting the polarizing films and the user. The entire optical shutter element serves as a multilayer compound that functions like a safety glass due to its multilayer structure of different materials.

The protective shield 7 serves to protect the ADF pane 10 from sparks and other emissions of the welding process. The protective shield 7 can be easily exchanged by the user, in particular without the use of tools to remove the protective shield 7. The protective shield 7 is shaped such that a plurality of protective shields 7 can be stacked on each other, nesting with each other such as to occupy little space when stored.

Figure 4A:
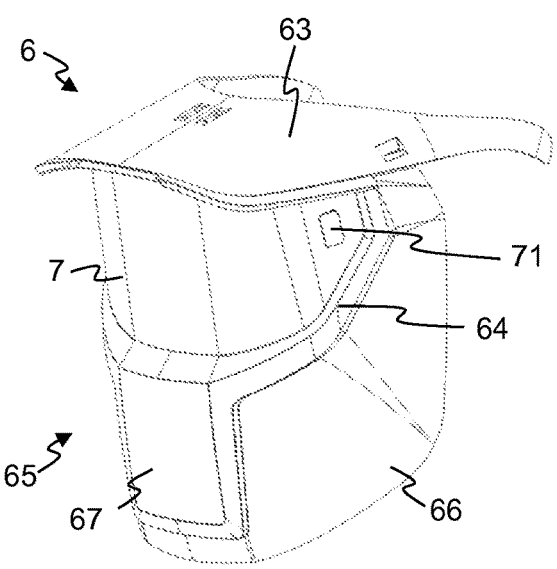
FIGS. 4a and 4b illustrate a shell part of the face protector.
Figure 4B:
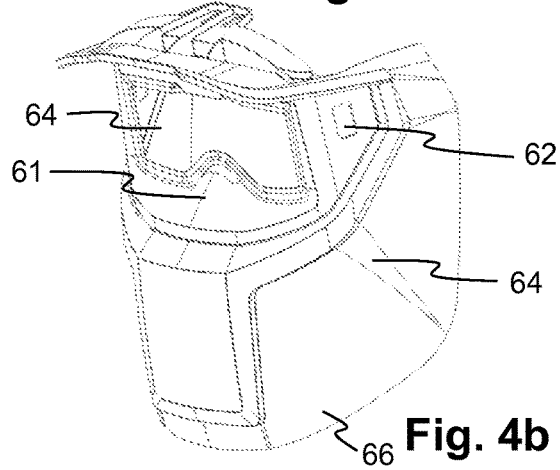

FIGS. 4a and 4b illustrate a shell 6 of the face protector by itself. The shell 6 is shaped as a single piece of plastic. It includes a frame with two essentially vertical side sections 64 joined at the top by an essentially horizontal transverse top section 63. The top section 63 is oriented essentially at a right angle to the side sections 64 and is joined to the side sections 64 along essentially horizontal edges. A front section 65 is joined to the side sections 64 along essentially vertical edges. As a result, the top, side and front sections form part of a box-like structure that gives the shell 6 structural stability. In addition, the front section 65 includes a convex section 67 that is curved in a convex shape, and a nose bridge 61 section that is shaped to extend at an angle to the convex section 67. This further stiffens the front section 65 and thus also the entire shell 6. The front section 65 includes a cutout or window section in which the ADF pane 10 is mounted.

The top section 63 is covered by the visor 46 and is shaped corresponding to the shape visor 46. This correspondence can be with regard to curvature of the top section 63 and the visor 46, and/or with regard to their contour. The top section 63 can include fastening elements for attaching the visor 46 to the top section 63. Such fastening elements also serve to transfer at least part of the force exerted by the weight of the shell 6 to the cap 4. The top section 63 can be detachable and can be part of a stiffener 47, shown in more detail in FIG. 13. FIG. 4a illustrates the shell 6 with the top section 63 and protective shield 7 in place, FIG. 4b illustrates the shell with these parts detached.

The neck protector 5 covers or overlaps with lower sections of the front section 65 and of the side sections 64. Lower sections 66 of the side sections are covered by corresponding side sections of the neck protector 5 and serve to distance the neck protector 5 from the user's neck, providing a ventilation space 44 that helps to aerate the face protector 1. The lower sections 66 of the side section are less important for the structural stability of the shell 6 as a whole and can be made of thinner material than the other sections of the shell 6.

Typical material thickness for the shell 6 and for the lower section 66 of the side section is between 1 mm and 2 mm, and in particular is 1.2 mm.

Figure 5:
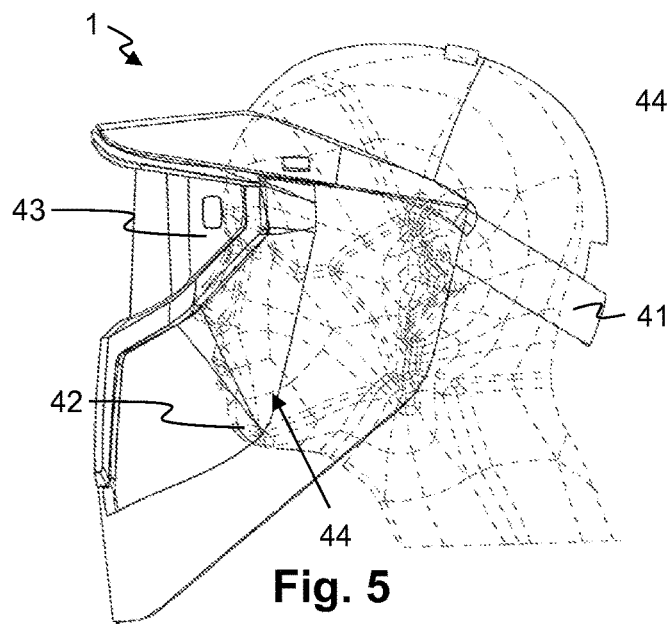

FIG. 5 is an elevation view of the face protector in relation to a user's or wearer's head. In addition to the parts already described, a head strap 41 is shown. The head strap 41 can be made of reinforced material and is arranged to take up part of the weight of the shell 6. The head strap 41 can be elastic or adjustable to the size of the wearer's head. Essentially (when the face protector 1 is worn) the remaining weight of the shell 6 is carried by the visor 46 which in turn is held by the crown 45 of the cap 4. This distributes the force exerted by the weight of the shell 6 over the user's head, making the face protector 1 comfortable to carry. In order to assist in this distribution of force, the cap 4 can include inserts (or stiffeners, braces, struts, reinforcements). Such stiffeners can be sewn into or attached to the cap 4 or inserted into corresponding openings provided in the cap 4.

Figure 13:
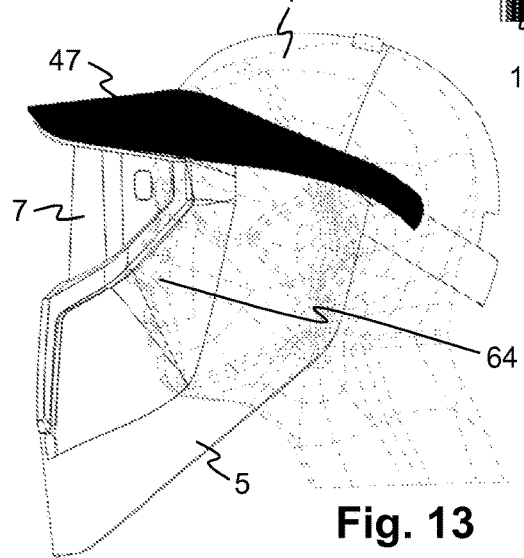
FIG. 13 illustrates a support element in the cap.

FIG. 13 is a schematic view of a stiffener 47 as part of the cap 4 (the shell 6 is not drawn). The stiffener 47 can be sewn into or otherwise attached to the cap 4. The stiffener 47 transfers and distributes forces acting on the visor 46 to side sections and optionally also back sections of the cap 4. The stiffener 47 typically is made of a plastic material but also can be made of metal.

The elevation view of FIG. 5 also shows a forehead space 43 between the visor 46, ADF unit 8 and the user's face, and a breathing space 42 between the front section 65 and the user's mouth and chin.

Figure 6:
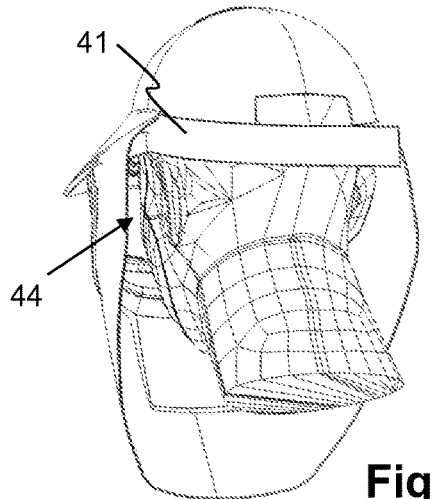
FIGS. 5 and 6 are views of the fact protector in relation to a user's head.

FIG. 6 is a view of the face protector in relation to a user's head from below and from the back. The ventilation space 44 created by the lower section 66 of the side section holding the neck protector 5 away from the user's neck is made visible.

Figure 7:
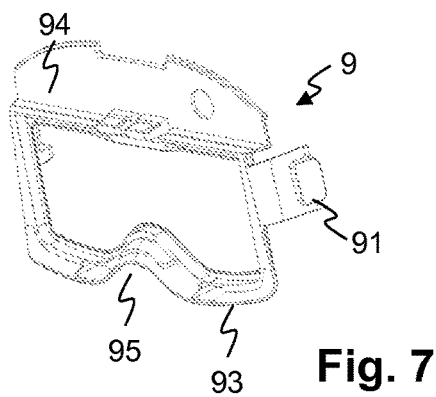
FIG. 7 illustrates an ADF frame.

FIG. 7 illustrates an ADF frame 9. The ADF frame 9 includes a frame section 93 that is designed to hold the ADF pane 10 against the shell 6, and a cover section 94 for covering and protecting the electronics unit 11. The frame section 93 includes a nose cutout 95 in its lower edge, corresponding to the location of the wearer's nose. The two sections 93, 94 can be integrally shaped, that is, shaped as a single piece. This typically is done by manufacturing the ADF frame 9 from a plastic material by an injection moulding or other moulding process. The ADF frame 9 further includes, at each side, a latch 91 which can assist in attaching the ADF frame 9 to the shell 6. The latch 91 too, can be integrally shaped with the other parts of the ADF frame 9. That is, the latch 91 can be shaped as a single piece with at least the frame section 93 and optionally also the cover section 94.

Figure 8:
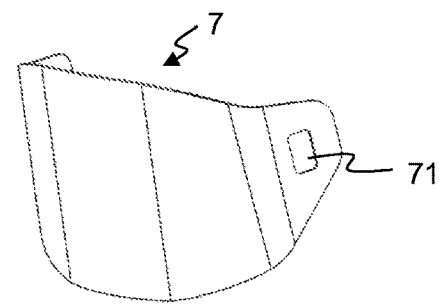
FIG. 8 illustrates a protective shield.

FIG. 8 illustrates a protective shield 7. The protective shield 7 includes a contoured bottom edge with a shape corresponding to that of the nose bridge 61 of the shell 6. Two lateral sections of the protective shield 7 include shield slots 71 for releasably attaching the protective shield 7 to the shell 6.

Figure 9:
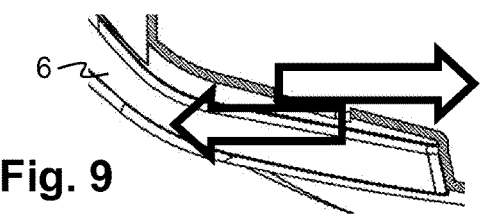
FIG. 9 is an elevation view of the shell.

FIG. 9 is an elevation view of the shell 6 in the region of one of the shell slots 62. Two arrows are shown, indicating the movement of forming tools that can used to form the shell 6, e.g. in an injection moulding process. There are no undercuts. The forming tools can thus be shaped without cams. Deforming, that is, separating the moulds, can be done by moving the moulds in the directions indicated by the arrows. The shafts of the arrows schematically indicate the shape of the moulds in the region of the shell slot 62.

Figure 10:
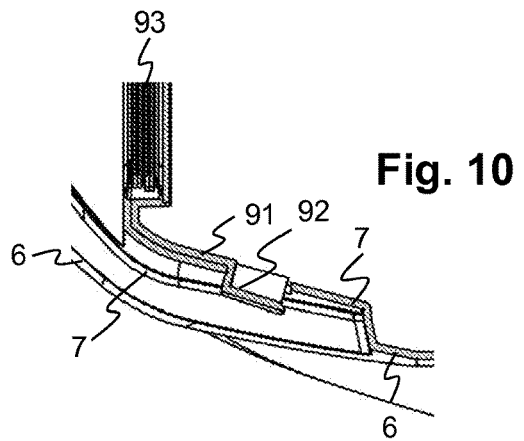
FIG. 10 is the same elevation view of the shell with the ADF frame and protective shield attached to the shell.

FIG. 10 is the same elevation view, with the ADF frame and protective shield 7 attached to the shell (for clarity, the ADF pane is omitted). The latch 91 reaches through the slot 62 of the shell 6 and then through the slot 71 of the protective shield 7, holding the protective shield 7 in place. For example, a hook 92 at an outer end of the latch 91 holds the protective shield 7 by the shield slot 71. The shell 6 and protective shield 7 can thus be manufactured from relatively stiff materials, and the latch 91 can be manufactured from a more resilient material, thereby allowing for a snap fit for attaching the protective shield 7 to the other parts of the hard shell unit 2.

Figure 11:
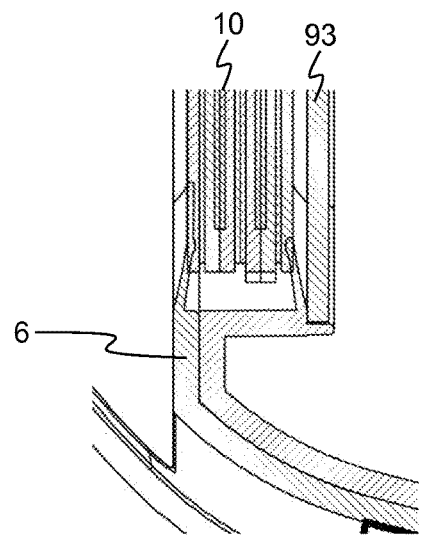
FIG. 11 is another elevation view of the sell with the ADF unit arranged between the shell and the ADF frame.

FIG. 11 is another elevation view showing the ADF unit 8 held between the shell 6 and the ADF frame 9. Around the circumference of the ADF unit 8, the shell 6 and the ADF frame 9 can be joined by gluing or welding such as, for example, ultrasonic welding or laser welding, etc. The joint can be profiled, as shown, with a groove in the ADF frame 9 and a rib on the ADF unit 8, or vice versa.

Figure 12:
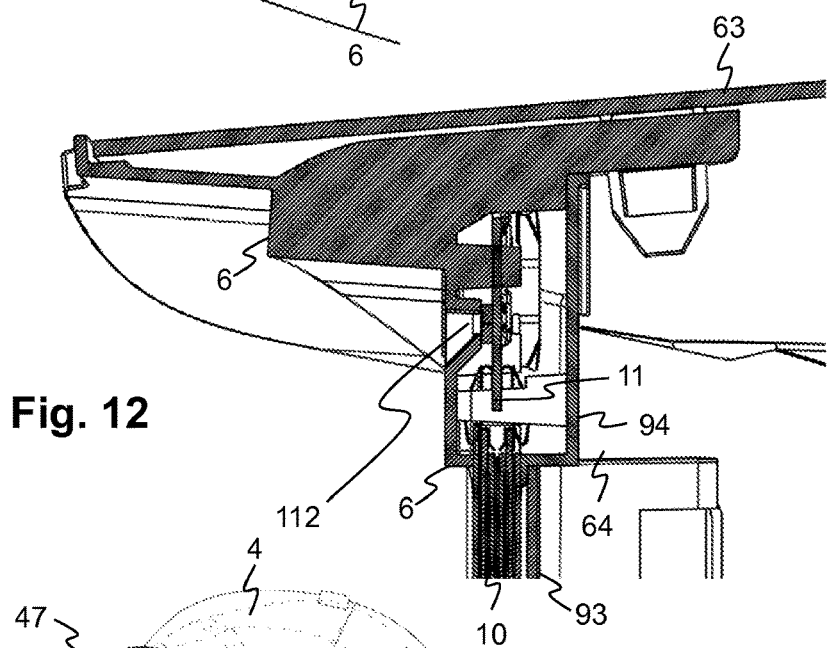
FIG. 12 is a plan view of the shell with the ADF unit and its electronics unit arranged between the shell and the ADF frame.

FIG. 12 is a plan view through the upper part of the ADF unit 8 and the ADF frame 9 and a corresponding part of the shell 6. The electronics unit 11 is enclosed between the cover section 94 of the ADF frame 9 and a corresponding part of the shell 6 located above the ADF pane 10. On the inside of the mask, operating elements such as a knob 111 operatively connected to the electronics unit 11 and also arranged on the electronics unit 11 pass through the cover section 94. Towards the outer side of the mask, a sensor 112 arranged on and operatively connected to the electronics unit 11 reaches at least partially through a corresponding opening in the shell 6. This allows the sensor 112 to capture light emitted by a welding operation, for automatically activating the ADF. The cover section 94 can be welded, by laser welding or ultrasonic welding, for example, or glued, or attached in another way to the shell 6, preferably forming a gas tight joint protecting the electronics unit 11.

Figure 14:
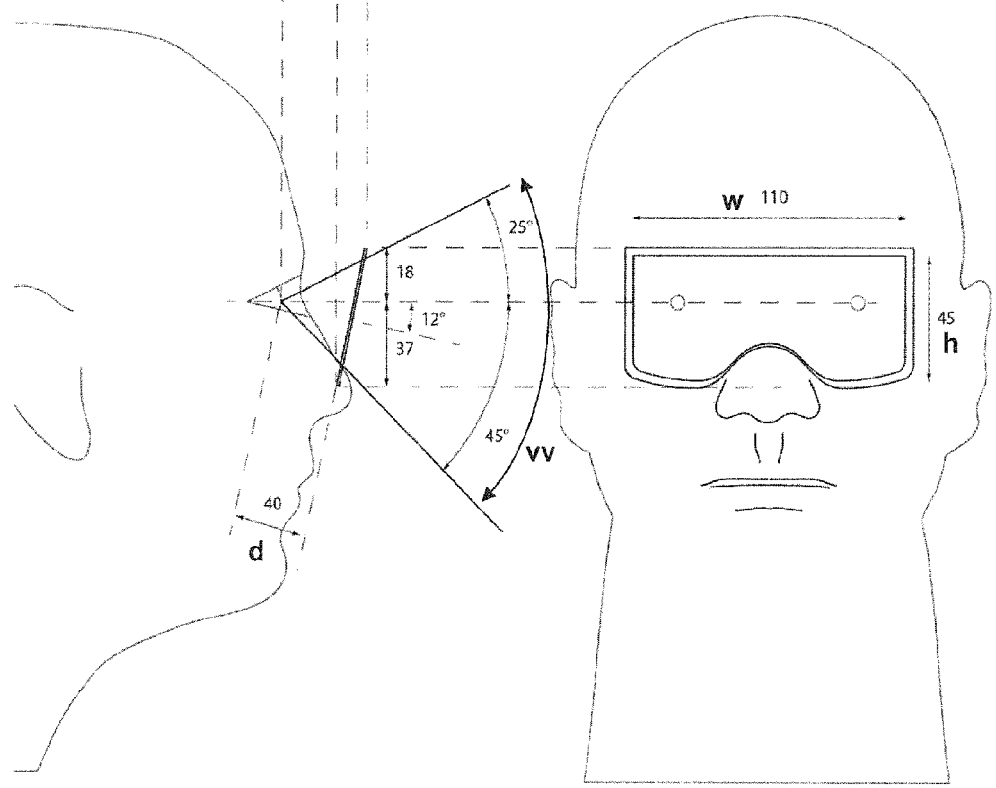
FIG. 14 is an illustration of the mask's field of view relative to a user's head.

FIG. 14 illustrates dimensions of the ADF pane 10 and the mask's field of view relative to a user's head. The distance from the wearer's pupils to the ADF pane 10 lies in the range of 30 mm to 50 mm, in particular in the range of 35 mm to 45 mm and more particularly at 40 mm. The vertical extension h of the (when in the transmissive state) transparent part of the ADF pane 10 is at least 40 mm, in particular at least 45 mm. The horizontal extension w of the transparent part of the ADF pane 10 is at least 100 mm, in particular at least 110 mm. As a result, a horizontal viewing angle vh for binocular viewing is at least 50°, in particular at least 60° (the viewing angle being computed for the average pupillary distance of 62 mm), and a vertical viewing angle vv is at least 60°, in particular at least 70°.

Compared to typical conventional welding masks, this is in increase of ca. two times 17.5°, that is ca. 35° in the horizontal direction, and of ca. 15° in the vertical direction.

Figure 15:
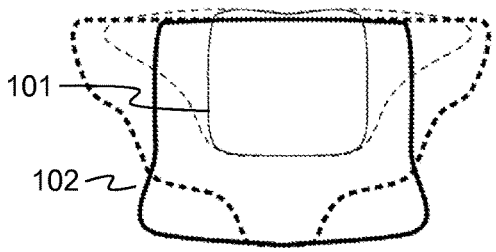
FIG. 15 is a comparison of fields of views.

FIG. 15 illustrates a comparison of fields of view for a typical welding mask, indicated by a smaller outline 101 and for a face protector as described herein, indicated by a larger outline 102. The field of view is increased by ca. 170%.

Figure 16:
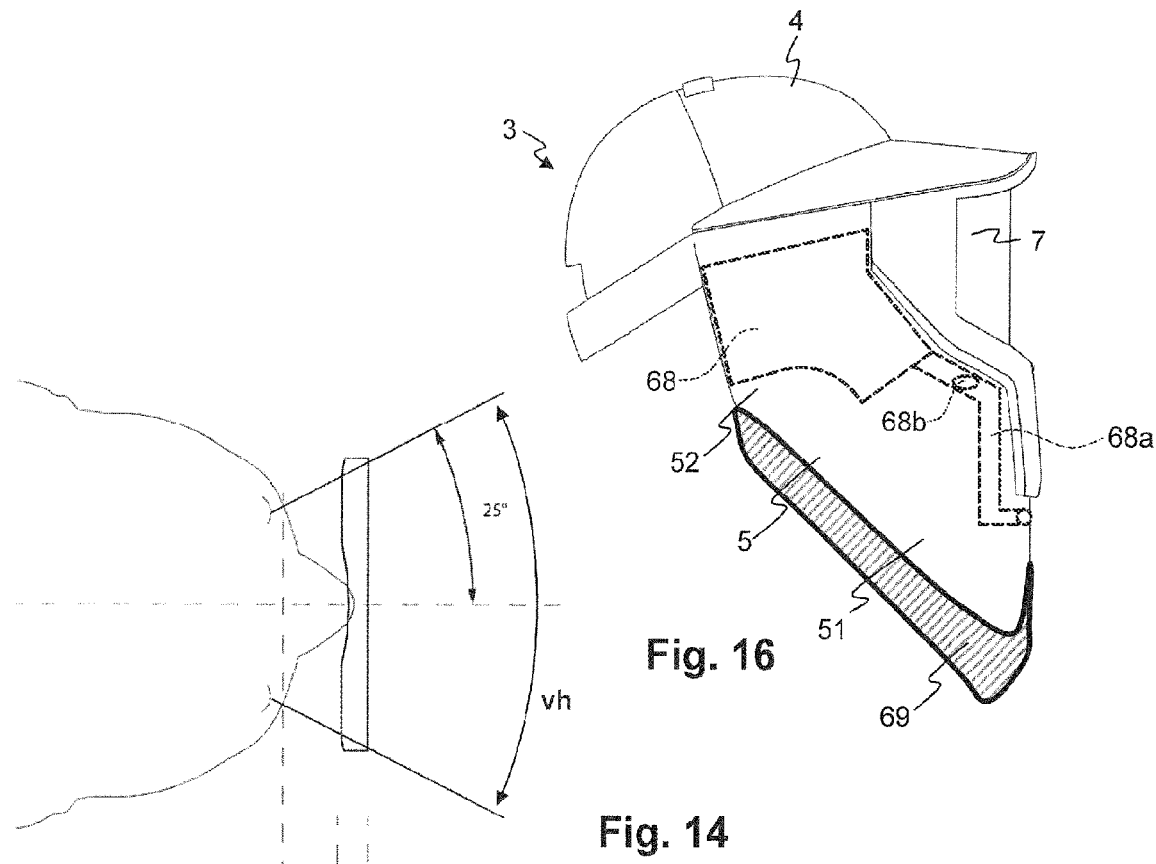
FIG. 16 illustrates inserts used as stiffener elements for a neck protector.

FIG. 16 shows the location of inserts 68 placed as stiffener elements between two layers of a base material (such as a textile or a flexible sheet of another type material) of the side sections of the neck protector 5. The inserts can be made of plastic. The inserts 68 can have a stiffness that is at least 5 times higher or at least 10 times higher than that of the side sections of the neck protector 5. The inserts 68 or at least part of the inserts can be located adjacent to the region of upper sections of the side sections 64 of the shell 6. The inserts 68 can span or cover and thereby stiffen at least 50% or 60% or 80% of an upper half 52 of a side section of the neck protector. The stiffeners prevent an upper section 52 of the neck protector 5 from being blown away by the blast of a fault arc while leaving a lower section 51 of the neck protector free to be pushed against the wearer's neck, together with lower sections 66 of the side section of the shell 6, which can be made of thinner material than the other sections of the shell 6, closing off the volume between the face protector and the wearer's neck and face.

While the invention has been described in present embodiments, it is distinctly understood that the invention is not limited thereto, but may be otherwise variously embodied and practised within the scope of the claims.

The invention claimed is:

1. A face protector for protecting a worker's eyes and face, comprising an auto-darkening filter unit, hereinafter referred to as an ADF unit, which, in turn, comprises a filter pane or ADF pane and an electronics unit driving the ADF pane, the electronics unit being configured to switch the ADF pane automatically from a transparent state to a darkened state when either one of a welding operation or a flash of a fault arc is detected, the face protector further comprising a hard shell unit and a soft shell unit attached to each other, the hard shell unit comprising a shell carrying the ADF unit with the ADF pane and being shaped to protect a wearer's face, the shell being manufactured of a plastic material, wherein the shell is shaped as a single piece of plastic and comprises a frame with two essentially vertical side sections joined at the top by an essentially horizontal transverse top section and a front section joined to the side sections along essentially vertical edges, wherein the top section is oriented essentially at a right angle to the side sections and is joined to the side sections along essentially horizontal edges;

the soft shell unit comprising a cap for protecting a top of the wearer's head and a neck protector for protecting a wearer's neck and formed from a flame retardant material, the cap comprising a visor, a rounded crown, and a stiffener, said stiffener extending rearwardly from the visor so as to transfer and distribute forces acting on the visor to side and back sections of the cap, the stiffener being made of a plastic or metal and extending at least partially around a horizontal circumference of the cap rearwardly toward a back of the cap and rearwardly beyond a highest part of the crown of the cap, both the cap and the neck protector of the soft shell unit being made of a combination of inherently flame retardant flexible fabric with support elements, wherein the top section of the shell of the hard shell unit comprises fastening elements for attaching the visor to the top section and wherein the neck protector extends at least around the front section and at least around the side sections of the shell of the hard shell unit carrying the ADF unit and wherein the neck protector covers and overlaps with lower sections of the front section and the side sections of the shell of the hard shell unit and wherein the lower sections of the side sections of the shell of the hard shell unit are covered by corresponding side sections of the neck protector.

2. The face protector of claim 1, wherein a lower edge of the ADF pane comprises a concave cutout for accommodating the wearer's nose.

3. The face protector of claim 1, wherein the face protector is configured such that when it is worn by a wearer, a distance from the wearer's pupils to the ADF pane lies in the range of 30 mm to 50 mm.

4. The face protector of claim 1, wherein a vertical extension of the transparent part of the ADF pane is at least 40 mm.

5. The face protector of claim 1, wherein a horizontal extension of the transparent part of the ADF pane is at least 100 mm.

6. The face protector of claim 1, wherein the ADF pane is curved, with side portions of the ADF pane, relative to a central portion of the ADF pane, curving backwards.

7. The face protector of claim 1, wherein the hard shell unit comprises an additional protective shield, the additional protective shield being attached via a releasable connection, the additional protective shield optionally being shaped such that a plurality of additional protective shields can be stacked on each other, nesting with each other.

8. The face protector of claim 1, wherein a top section, two side sections and a front section of the shell form a box-like structure that gives the shell structural stability, and wherein the front section comprises a convex section that is curved in a convex shape, and a nose bridge section that is shaped to extend at an angle to the convex section, further stiffening the front section.

9. The face protector of claim 1, wherein the electronics unit is mounted on the shell via a cover section of an ADF frame, the cover section being attached to, in particular glued or welded to, the shell and holding the electronics unit in position between the cover section and the shell.

10. The face protector of claim 1, wherein the neck protector and the shell are affixed to each other, without gaps as a closed design.

11. The face protector of claim 1, wherein the lower sections of the side sections of the shell of the hard shell unit covered by the neck protector are made of thinner material than the other sections of the shell.

12. The face protector of claim 1, wherein the neck protector comprises plastic stiffener elements that are joined to a flexible base material of the neck protector, wherein the stiffener elements are plastic stiffer than the base material of the neck protector.

13. The face protector of claim 12, wherein the plastic stiffener elements are joined to the flexible base material of the neck protector by placing them between two layers of the flexible base material of the neck protector.

14. The face protector of claim 1, wherein the cap comprises the rounded crown that fits on a wearer's head and the visor that rostrally extends from the rounded crown at least partially in line of sight of a wearer, wherein the visor covers a transverse top section of the shell, the top section protecting a forehead space enclosed by the hard shell unit, and the visor supporting at least some of the weight of the hard shell unit when the face protector is worn by a wearer.

15. The face protector of claim 14, wherein the stiffener is sewn in or attached to the cap, the stiffener holding up the visor against at least part of the weight of the hard shell unit.

16. The face protector of claim 1, wherein the shell of the hard shell unit comprises lateral side sections, a lower section of each lateral side section being shaped to keep the neck protector spaced from the wearer's neck, thereby establishing a ventilation space between the neck protector and the wearer's neck, the lateral side sections being covered by the neck protector.

17. The face protector of claim 16, wherein the lower sections of the lateral side sections are made of thinner material than the remaining sections of the lateral side sections, and optionally also thinner than the other sections of the shell.

18. The face protector of claim 17, wherein the ADF pane is mounted on the shell via a frame section of an ADF frame, the frame section being attached to the shell and holding the ADF pane in position between the frame section and the shell.

19. The face protector of claim 18, wherein the ADF frame comprises at least one latch, the ADF frame is mounted at the inside of the shell with the latch reaching through a slot of the shell and forming a snap fit with the protective shield, holding the protective shield in place on the outer side of the shell.

20. The face protector of claim 19, wherein at least the frame section and the latch are integrally shaped as a single piece.

* * * * *